US006273872B1

United States Patent
Friedman

(10) Patent No.: US 6,273,872 B1
(45) Date of Patent: Aug. 14, 2001

(54) POST SURGICAL BELT

(76) Inventor: Dawn G. Friedman, 1420 Peerless Pl. #102, Los Angeles, CA (US) 90035

( * ) Notice: Subject to any disclaimer, the term of this patent is extended or adjusted under 35 U.S.C. 154(b) by 0 days.

(21) Appl. No.: 09/257,287

(22) Filed: Feb. 25, 1999

(51) Int. Cl.$^7$ ..................................... A61M 5/32
(52) U.S. Cl. ..................... 604/174; 604/345; 224/665
(58) Field of Search ..................... 604/317, 332, 604/322, 345, 327, 174, 179; 224/600, 601, 605, 625, 620, 665

(56) References Cited

U.S. PATENT DOCUMENTS

| D. 393,310 | 4/1998 | Russo . |
| 2,697,436 | 12/1954 | Coston . |
| 2,727,512 | 12/1955 | Muller . |
| 3,812,851 | 5/1974 | Rodriguez . |
| 4,249,529 | 2/1981 | Nestor et al. . |
| 4,359,053 | 11/1982 | Benjamin . |
| 5,076,289 | 12/1991 | Darling . |
| 5,087,251 | * 2/1992 | Heyman et al. ............... 604/327 |
| 5,098,399 | 3/1992 | Tollini . |
| 5,098,420 | * 3/1992 | Iacone ............................. 604/338 |
| 5,234,420 | * 8/1993 | Horton et al. .................. 604/345 |
| 5,336,179 | 8/1994 | Ryan . |
| 5,338,315 | * 8/1994 | Baker ............................. 604/395 |
| 5,643,233 | 7/1997 | Turner . |
| 5,774,950 | 7/1998 | Stout . |

OTHER PUBLICATIONS

*MAMM*, Letters to the Editor, "The Bra Pouch," May 1999.

* cited by examiner

*Primary Examiner*—Richard K. Seidel
*Assistant Examiner*—Kevin C. Sirmoas
(74) *Attorney, Agent, or Firm*—Blakely, Sokoloff, Taylor & Zafman

(57) ABSTRACT

The invention relates to an apparatus to support a post operative device. In one embodiment, a belt is provided for circumferential attachment about a segment of a body and at least one loop detachably coupled to the belt and freely moveable along a portion of the belt defining a circumference, the loop to receive and hold a post surgical drainage device.

11 Claims, 2 Drawing Sheets

POST SURGICAL BELT

BACKGROUND OF INVENTION

1. Field of Invention

The invention relates to an apparatus to support medical devices retained by post operative patients. More particularly, the invention relates to a post surgical belt with at least one adjustable loop to support a post operative device.

2. Background of the Invention

Various surgical procedures require continual drainage of the affected area well into the post operative recovery period. Of great importance to patients is the ability to have some mobility after surgery and to reduce the inconvenience caused by the ongoing drainage. Previously, such surgical implants, fluid receptacles and related devices were retained to the patient using tape and/or adhesive to secure the devices to their bodies, with resultant discomfort and restriction of movement. Allergies to the adhesive or skin irritation were also potential problems. Other methods for support included clipping or pinning the devices to underwear or outer clothing. As with the adhesive, however, the limitations on movement and the resulting discomfort of restricting outer garments as well as general inconvenience when the desired location for the device could not be easily reached or accommodated were all drawbacks to these methods.

BRIEF SUMMARY OF THE INVENTION

An apparatus to support a post operative device attached to a body or body segment is disclosed. In one embodiment, a belt is circumferentially attachable about a segment of a body and at least one loop is detachably coupled to the belt and freely movable along a portion of the belt along the circumference. The loop may receive and hold a post surgical evacuator drainage device.

DETAILED DESCRIPTION OF THE INVENTION

For most patients the rigors of surgery and the accompanying hospitalization are difficult enough without having also to retain implants and wear receptacles to hold fluids during the post-operative period. Such difficulties and potential embarrassment obviously significantly impact the healing process; while a support apparatus which does not impede the patient's ability to independently carry out daily activities, obviously assists the patient's recovery. Thus, a convenient support apparatus such that provides for easy adjustment so as to allow maximum comfortable wear and less restricted movement as well as discreet placement under the patient's garments is desirable.

Figure 1:
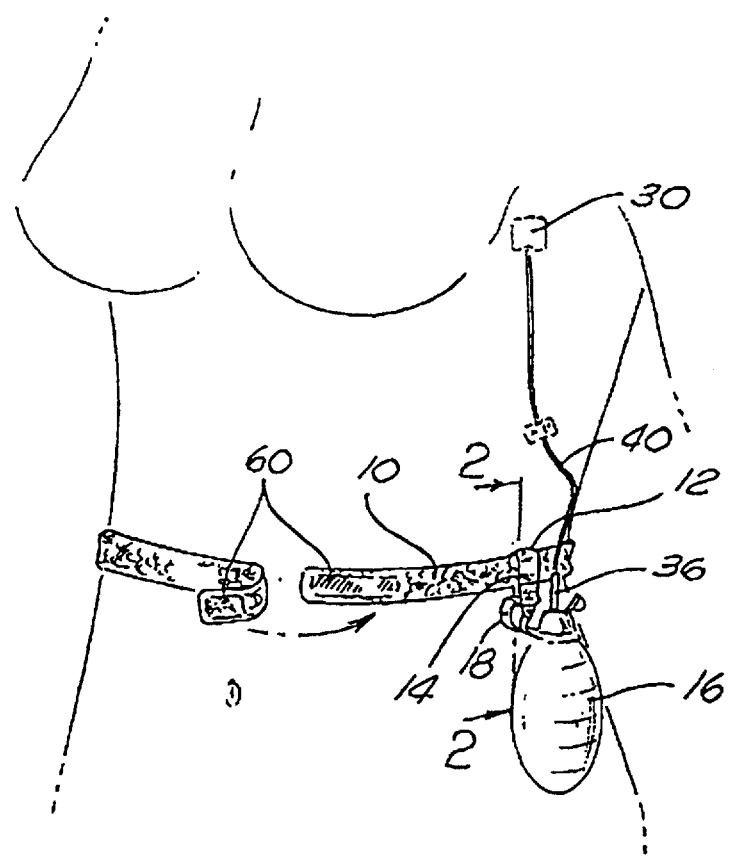
FIG. 1 is a perspective view of one embodiment of the apparatus as attached to a patient.

FIG. 1 shows a perspective view of an embodiment of the post surgical belt worn by a post operative patient having a surgically implanted drainage system. The belt 10 is wrapped around a body segment, here the waist, so as to allow collection of fluid from surgical incision site 30. The conduit 40 transfers the fluid drained to the receptacle 16, through a conduit connection therewith 36. A loop 12 attached around belt 10 by a fastener 14, which may be a snap fastener, an interlocking fabric surface fastener (such as hook and loop material available under the trademark VELCRO® from Velcro Industries B.V. of the Netherlands) or other fastener type allowing the loop 12 to be freely detachable from the belt 10. An integral loop 18 connected to the receptacle 16 allows its attachment to the loop 12. In this embodiment, the loop 12 is freely movable along a portion of the circumference of the belt 10 allowing the receptacle 16 to be moved and adjusted for comfort or discreet placement along substantially the entire circumference of the belt 10. While this figure pictures only one loop, other embodiments including multiple loops attached to the belt are within the scope and contemplation of this invention.

While in this embodiment, the belt supports a post operative drainage receptacle, it is also within the scope and contemplation of this invention that the belt also receive and support other medical devices for the infusion or delivery of medicine, blood, nutrient, and the like. In this embodiment, pictured in FIG. 1, since a drainage receptacle 16 must be worn at all times, it is important that the belt provide maximum comfort. To that end, soft breathable material such as cotton terry cloth has been found suitable. Unfortunately, terry cloth becomes waterlogged during normal bathing.

However, because the loop 12 supporting the receptacle 16 may be detached from the belt 10, the belt may be removed and a new (dry) belt substituted by the patient after a bath or shower thereby ameliorating any waterlogging problem. In one embodiment, the loop 12 resists fluid absorption allowing its immersion in, or contact with water or water/soap emulsions without retaining fluid. As stated previously, other embodiments of this invention may employ multiple loops with similar fluid resistant properties. Such loops may be rubber, latex, thermoplastic or any other bio-compatible non-absorbent material. It is also within the scope and contemplation of the invention for the belt to also be made of non-absorbent material, such as thermoplastic, to avoid the need to change the belt after the patient bathes or showers.

The belt itself may be fastened around the patient by ordinary methods known in the art. In one embodiment the fastening device is VELCRO®, fastened in the front of the patient 60. Other embodiments may use snap fasteners, buckles, ties or other methods, and may allow side or rear fastening or gradual tightening. While the embodiment of FIG. 1 is attached about the waist, other uses and embodiments may be attached to other segments of the body. Accordingly, it is within the scope and contemplation of the invention for the belt to be suitable for attachments about a leg, or arm or about the thighs or higher on the torso, for instance below the breasts and under the arms at the armpit. Depending on the body segment to be encompassed, the size of belts, loops and/or receptacles may vary.

Figure 2:
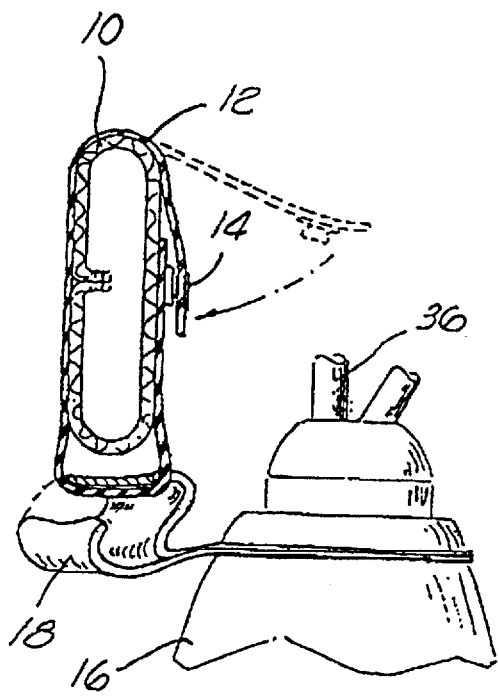
FIG. 2 is a cross-sectional view of one embodiment showing the drainage receptacle as attached to the loop surrounding the belt.

Referring to FIG. 2, this illustrates a cross-section of the belt and attached loop in a particular embodiment. Here the receptacle 16 includes a projecting integral appendage 18 which may be used to couple the receptacle 16 to the loop 12 as the loop 12 is detachably affixed around the belt 10 by a snap fastener 14 engaging at roughly the two ends of the material that makes up the loop 12. VELCRO® or other fastening means known in the art may also be used to affix the loop about the belt in other embodiments.

Figure 2A:
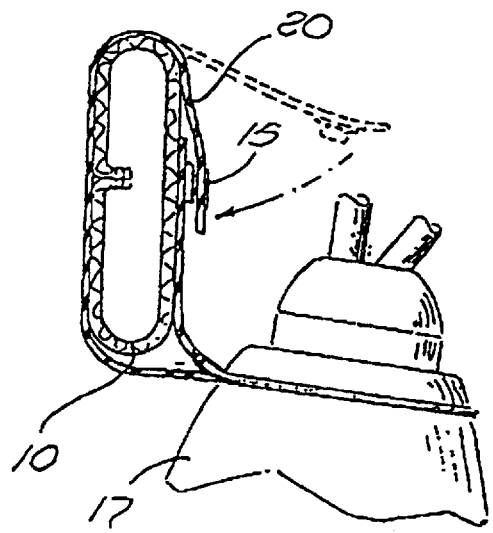
FIG. 2A is a cross section of one embodiment wherein the receptacle has a reclosable loop integral therewith.

Referring to FIG. 2A, this illustrates a separate embodiment wherein the receptacle 17 includes an integral loop extension 20 formed as a part of the receptacle 17 having a fastener 15 to detachably secure the loop extension 20 to itself around the belt and allowing it to be freely removed from and reattached thereto. The receptacle and its integral loop extension may be molded from a single material, such as commonly available, thermoplastics. As with the embodiment of FIG. 2, the fastener allowing the detachment of the loop extension (and hence the integral receptacle) is pictured as a snap fastener 15. Other fasteners such as VELCRO® or reusable adhesive may also be utilized.

Figure 3:
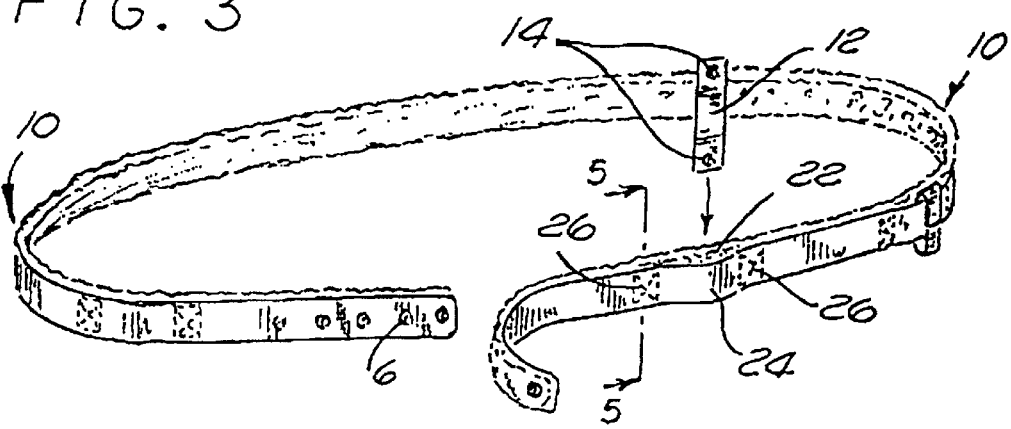
FIG. 3 is a perspective view of the post surgical belt of one embodiment of the invention.

FIG. 3 is a perspective view of one embodiment. In this embodiment, the belt 10 is composed of two separate co-extensive layers extending along a substantial portion of the length of the belt. Inner layer 22 which may contact the patient's skin, can be made of a soft material which may be both breathable and absorbent. As contrasted with many plastic or rubber (including latex) materials, which often cause irritation due to limited porosity, these qualities (breathability and absorbency) promote greater comfort for the patient in wearing the belt. In one embodiment this soft breathable and absorbent material is terry cloth. The outer layer 24 may also be terry cloth, or it may be a durable synthetic fabric such as nylon. Other suitable materials will occur to one of ordinary skill in the art.

Outer layer 24 is affixed to inner layer 22 at a plurality of attachment points 26. In one embodiment the means of affixation is by cross stitching at the attachment points 26, other means known in the art such as adhesive, single stitching or snaps etc. may also be used and are within the scope and contemplation of the invention. The loop 12 is fastened around the outer layer 24, in this embodiment by snap fasteners, so as to be freely movable along a length of the belt defined between the attachment points 26 which bind the outer layer 24 to the inner layer 22. Spacing of the attachment points along the belt outer layer 24 determines the distance through which the loop 12 may move along the belt 10. More narrowly spaced attachment points 26 increase structural stability as more loops 12 and drains are attached to the belt but reduce the arc through which any particular loop 12 may move. The increased stability may allow the belt assembly to accommodate more than one loop and receptacle on the belt, as shown in this embodiment. Alternatively the spacing may be set at longer intervals to allow for a greater traversal arc for placement of the receptacle. In one embodiment where the belt encompasses the patient's waist, by situating two attachment points 26 on the belt, each just to the right and left, respectively, of the frontal belt fastener 60 along with situating another attachment point approximately diametrically opposite the front fastener, on the patient's mid-back, a traversal arc of about 180° along the belt circumference may be created for the loop and/or attached receptacle. Because this allows a user to attach the loop at the front of the belt and slide it around to the side or back, ease of use is improved over systems that require the user to attach the device at its ultimate use location.

While the outer layer 24 engages the loop 12 and receptacle, the inner layer 22 provides a protective surface interposed between the loop 12 and the patient's skin to avoid irritation from contact or friction with the loop 12. In one embodiment, soft terry cloth avoids or minimizes this friction or irritation. This is particularly desirable where the loops 12 are made of non-breathable materials such as latex, rubber, thermoplastic or other synthetic materials.

Figure 4:
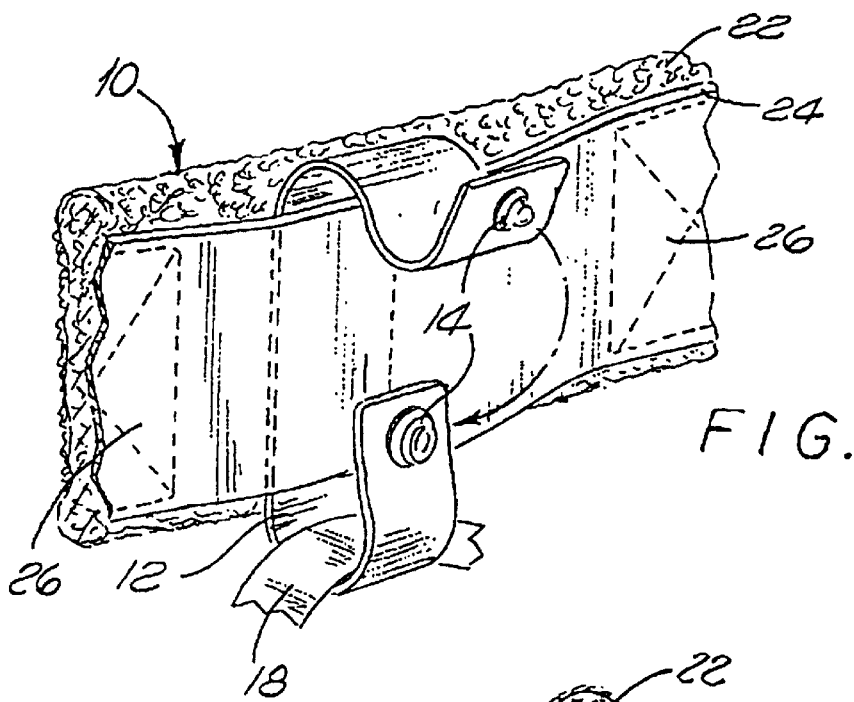
FIG. 4 is a partial sectional view of a belt of an alternative embodiment of the invention.

Referring to FIG. 4, this illustrates a close up view of the loop 12 attached by snap fasteners 14 about the belt outer layer 24 with the belt inner layer 22 disposed between the loop 12 and the wearer's skin or inner garments. Attachment points 26, depicted in this embodiment as cross-stitching define the traversal distance of the loop 12 along the outer layer 24. The receptacle is attached to the loop 12 in this embodiment by its projecting integral appendage 18 as shown in FIG. 2.

Figure 5:
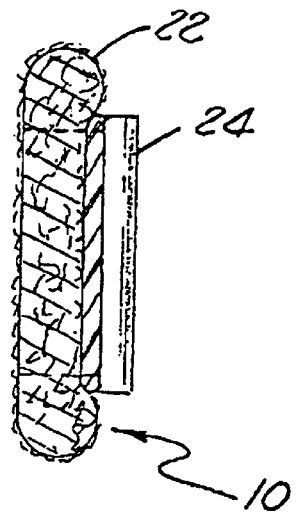
FIG. 5 is a sectional view of the belt of FIG. 4.

Referring to FIG. 5, this illustrates a cross-section of one embodiment of the belt 10 comprised of an inner layer 22 and an outer layer 24 to which the loop will be attached and along which the loop will be freely moveable within the distance between attachment points. As previously stated, the attachment points may be placed at variable distances to either allow for the attachment of multiple drainage devices about the belt circumference and/or to regulate the traversal distance of such devices as desired.

In the preceding detailed description, the invention is described with reference to specific embodiments thereof. It will, however, be evident that various modifications and changes may be made thereto without departing from the broader spirit and scope of the invention as set forth in the claims. The specification and drawings are accordingly, to be regarded in an illustrative rather then restrictive sense.

What is claimed is:

1. An apparatus comprising:
   a belt circumferentially attachable about a body segment;
   a first layer defining a portion of the outer circumference of the belt;
   a second layer defining a portion of the inner circumference of the belt;
   a plurality of attachment points disposed along the outer circumference of the belt coupling the first layer to the second layer, wherein the first and second layers are manually detachable such that a spare layer may be substituted for either the first or the second layer; and
   a post operative device having an integrally formed loop with an disengageable fastener coupled around the first layer and freely movable along a portion of the outer circumference defined by the first layer between a pair of attachment points, the post operative device being freely removable therefrom by disengagement of the fastener.

2. The apparatus of claim 1, wherein the first layer resists absorption of liquid.

3. The apparatus of claim 1, wherein the second layer is made of breathable absorbent material and shields the body from loop contact when the belt is circumferentially attached around the body segment.

4. The apparatus of claim 1, wherein the integrally formed loop and post operative device resist absorption of liquid.

5. The apparatus of claim 1, wherein the post operative device is a fluid receiving receptacle.

6. An apparatus comprising:
   a belt attachable circumferentially about a segment of a body; and at least one discrete loop, detachably coupled to the belt and freely moveable along a portion of the belt defining a circumference, the at least one loop to receive and hold a post surgical device;
   a first layer defining a portion of the outer circumference of the belt;
   a second layer defining a portion of the inner circumference of the belt; and
   wherein the first and second layers are manually detachable such that a spare layer may be substituted for either the first or the second layer.

7. The apparatus of claim 6, wherein the belt has an inner and outer circumference and further comprises:
   a plurality of attachment points disposed along the outer circumference for the belt coupling the first layer to the second layer such that the first layer and second layer are separable between attachment points.

8. The apparatus of claim 7, wherein the loop is detachably coupled to the belt around the first layer and is freely moveable along a portion of the outer circumference defined by the first layer between a pair of attachment points.

9. The apparatus of claim 7 wherein the first and second layers are manually detachable such that a spare layer may be substituted for either the first or the second layer.

10. The apparatus of claim 6, wherein the second layer is made of breathable absorbent material and shields the body from loop contact when the belt is circumferentially attached about the body segment.

11. The apparatus of claim 6, wherein the first layer resists absorption of liquid.

* * * * *

UNITED STATES PATENT AND TRADEMARK OFFICE
CERTIFICATE OF CORRECTION

PATENT NO. : 6,273,872 B1  Page 1 of 1
APPLICATION NO. : 09/257287
DATED : August 14, 2001
INVENTOR(S) : Friedman It is certified that error appears in the above-identified patent and that said Letters Patent is hereby corrected as shown below:

Title Page, Item [56], Other Publications, delete "Sirmoas" and insert -- Sirmons --.

Signed and Sealed this

Twenty-first Day of August, 2007

JON W. DUDAS
*Director of the United States Patent and Trademark Office*